United States Patent
Yamada et al.

(10) Patent No.: US 11,104,643 B2
(45) Date of Patent: *Aug. 31, 2021

(54) BISMALEIMIDE MODIFIED PRODUCT AND METHOD FOR PRODUCING THE SAME

(71) Applicant: UNITIKA LTD., Amagasaki (JP)

(72) Inventors: Yuki Yamada, Uji (JP); Tatsuya Morikita, Uji (JP); Takeshi Yoshida, Uji (JP); Akira Shigeta, Uji (JP); Yoshiaki Echigo, Uji (JP)

(73) Assignee: UNITIKA LTD., Amagasaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/930,397

(22) Filed: Jul. 16, 2020

(65) Prior Publication Data

US 2020/0354317 A1 Nov. 12, 2020

Related U.S. Application Data

(63) Continuation of application No. 16/011,077, filed on Jun. 18, 2018, now Pat. No. 10,759,753.

(30) Foreign Application Priority Data

Jun. 19, 2017 (JP) .............................. JP2017-119655

(51) Int. Cl.
*C07D 207/448* (2006.01)

(52) U.S. Cl.
CPC ................................ *C07D 207/448* (2013.01)

(58) Field of Classification Search
None
See application file for complete search history.

(56) References Cited

U.S. PATENT DOCUMENTS

| | | | |
|---|---|---|---|
| H424 H | 2/1988 | Martin et al. | |
| 5,198,515 A | 3/1993 | van Swieten et al. | |
| 6,281,314 B1 | 8/2001 | Tong et al. | |
| 10,759,753 B2 * | 9/2020 | Yamada | C07D 207/448 |
| 2008/0262191 A1 | 10/2008 | Mizori | |

FOREIGN PATENT DOCUMENTS

| | | |
|---|---|---|
| JP | 10-505599 A | 6/1996 |
| JP | 2008-13772 A | 1/2008 |
| JP | 2012-117070 A | 6/2012 |
| JP | 2015-193725 A | 11/2015 |
| JP | 2017-31227 A | 2/2017 |
| JP | 2017-48391 A | 3/2017 |
| JP | 2018-24747 A | 2/2018 |
| JP | 2018-83883 A | 5/2018 |
| WO | WO 98/07891 A2 | 3/1998 |
| WO | WO 2004/099331 A2 | 11/2004 |

\* cited by examiner

*Primary Examiner* — Joseph R Kosack

(74) *Attorney, Agent, or Firm* — Birch, Stewart, Kolasch & Birch, LLP

(57) ABSTRACT

An object of the present invention is to provide a bismaleimide (D-BMI) modified product in which an amino group of dimer diamine (DDA) is maleimidized, which has the good heat resistance, and has the sufficiently enhanced processability, and a method for producing the same. There are provided:

<1> A bismaleimide (D-BMI) modified product in which an amino group of dimer diamine is maleimidized, the bismaleimide modified product having the following characteristics:
1) An acid value of the D-BMI modified product is 2 mg-KOH/g or less.
2) In $^1$H-NMR, when quantitative comparison is performed using an integrated value (A) of a peak corresponding to a proton of a methylene group directly bound to a nitrogen atom of a maleimide group and an integrated value (B) of a peak corresponding to a vinyl proton of a maleimide group, A/B is 1.25 or more and 2.00 or less.

<2> A method for producing D-BMI, the method including the following steps:
1) A step of preparing a crude D-BMI solution having an acid value of more than 2 mg-KOH/g.
2) A step of lowering an acid value of D-BMI to 2 mg-KOH/g or less by reacting an acid component in the solution with a carbodiimide compound.
3) A step of reacting the solution without a catalyst at 110 to 200° C. in a solvent.

1 Claim, 2 Drawing Sheets

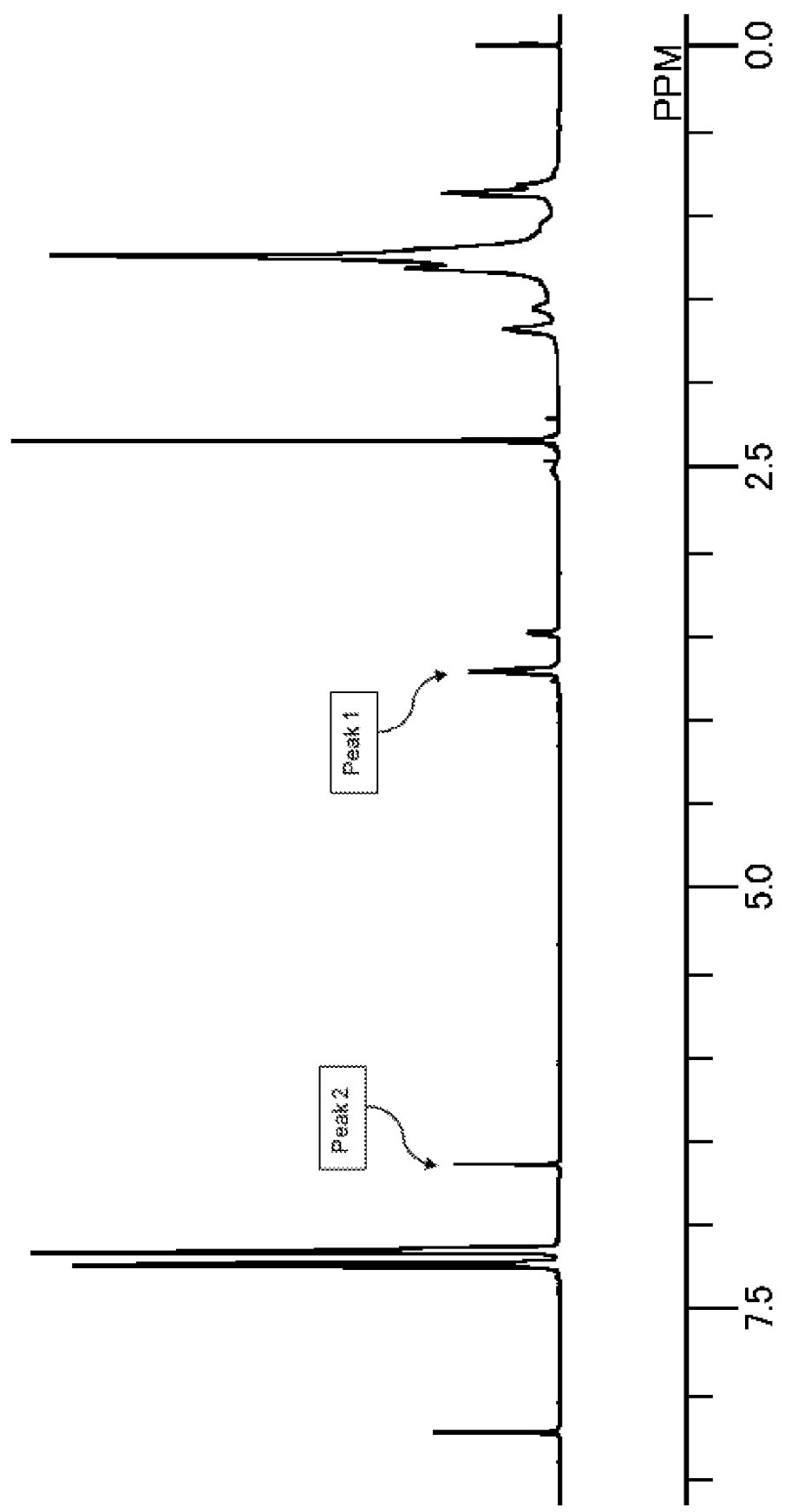
[Fig.1]

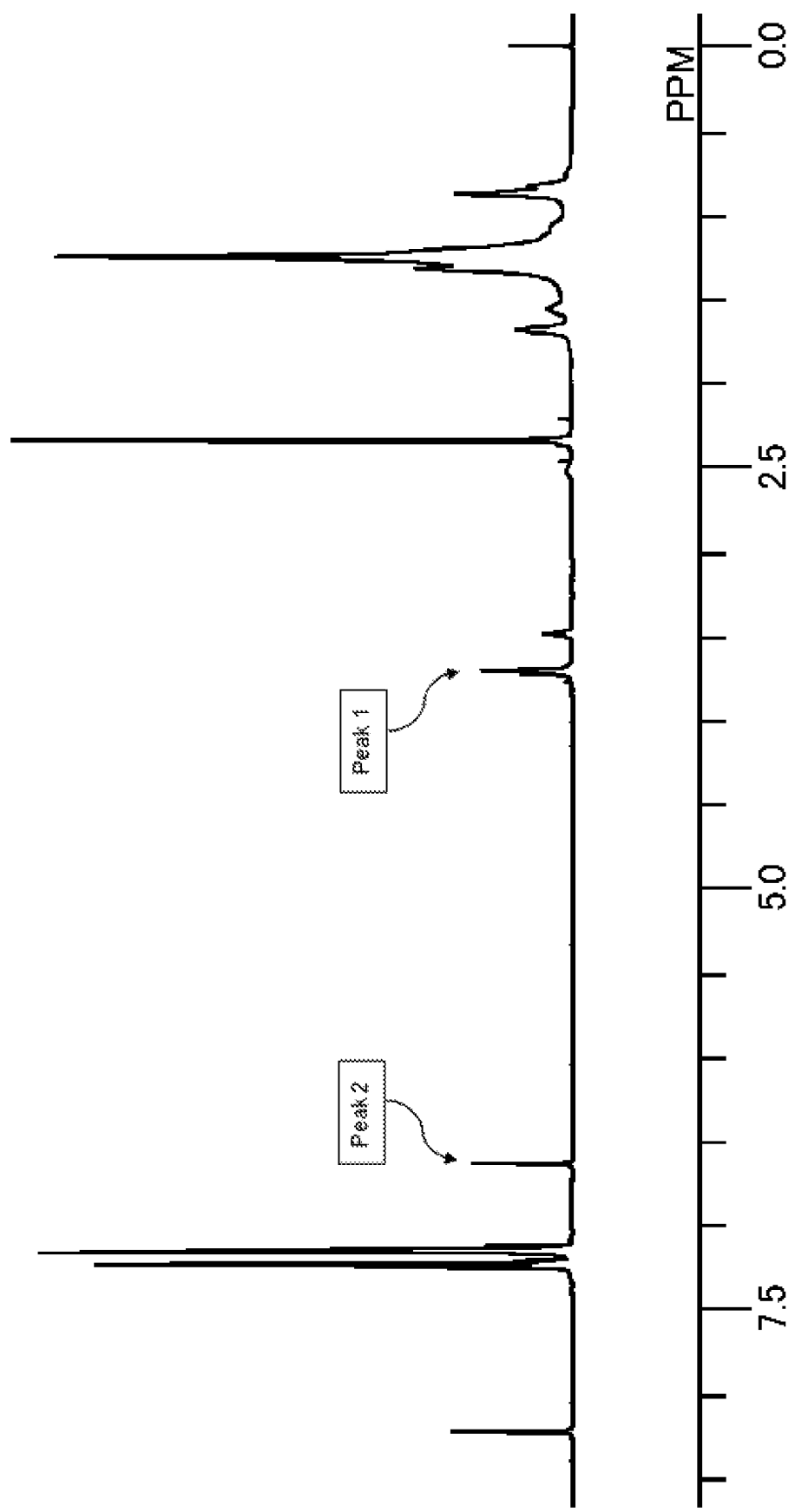
[Fig.2]

BISMALEIMIDE MODIFIED PRODUCT AND METHOD FOR PRODUCING THE SAME

CROSS-REFERENCE TO RELATED APPLICATION

This application is a Divisional application of application Ser. No. 16/011,077, filed on Jun. 18, 2018, which claims the benefit under 35 U.S.C. § 119(a) to Patent Application No. 2017-119655, filed in Japan on Jun. 19, 2017, all of which are hereby expressly incorporated by reference into the present application.

ART FIELD RELATED

The present invention relates to a bismaleimide modified product and a method for producing the same.

PRIOR ART

High-density integration, high-density implementation, and the like of electronic parts used in electronic devices such as cellular phones, smartphones, and notebook-sized personal computers have proceeded. As a resin material such as an adhesive and a sealing material used in these electronic parts, a material that has a low water absorption rate, is excellent in reliance, and is heat-resistant is required. A method using, as a component of a composition used in these adhesives, sealing materials, and the like, maleimide (D-BMI) in which an amino group of dimer diamine (aliphatic diamine derived from dimer acid having 24 to 48 carbon atoms; hereinafter, abbreviated as "DDA" in some cases) is maleimidized is known. For example, Patent Document 1 discloses a method using D-BMI as a component of an adhesive composition for implementing a LED element. Patent Document 2 discloses a method using D-BMI as a component of an anisotropic electrically conductive adhesive component for a printed circuit board. Patent Documents 3 and 4 disclose a method for using D-BMI as a component of a solid composition for sealing a semiconductor.

D-BMI can be obtained by the known methods disclosed in Patent Documents 5 to 10, and the like. That is, D-BMI can be produced, for example, by reacting diamine and maleic anhydride in a solvent under an acid catalyst to give maleamic acid (hereinafter, abbreviated as "MAA" in some cases), thereafter, maleimidizing maleamic acid with an acid catalyst or the like (ring closure by dehydration) to obtain a crude BMI solution, and purifying the solution. Additionally, these D-BMIs are also marketed from Designer Molecules Inc. (hereinafter, abbreviated as "DMI company" in some cases) under a trade name such as BMI-689, BMI-1500, BMI-1700, and BMI-3000.

[Patent Documents]
[Patent Document 1] JP-A No. 2017-31227
[Patent Document 2] JP-A No. 2015-193725
[Patent Document 3] JP-A No. 2018-24747
[Patent Document 4] JP-A No. 2018-83893
[Patent Document 5] US Statutory Invention Registration No. H424
[Patent Document 6] U.S. Pat. No. 6,281,314
[Patent Document 7] US Patent Application Publication No. 20080262191
[Patent Document 8] JP-T No. 10-505599
[Patent Document 9] JP-A No. 2008-13772
[Patent Document 10] JP-A No. 2012-117070
[Patent Document 11] JP-A No. 2017-48391

DISCLOSURE OF INVENTION

Technical Problems to be Solved by the Invention

However, since even when the known D-BMI (including commercial products) has been purified, an acid component such as MAA in which maleimide rings have not yet formed, fumaramic acid, and a Michael adduct (compound generated by further reacting a compound generated by a Michael addition reaction of amine to MAA, with maleic anhydride) remains at a very small quantity, an acid value considerably exceeds 2 mg-KOH/g, and D-BMI having an acid value of 2 mg-KOH/g or less has not been known.

When D-BMI containing such a remaining acid component is used, for example, as a component of a solid sealing material of a semiconductor, a problem such as moisture absorption and corrosion is caused in some cases. Additionally, due to this acid component, the heat resistance is deteriorated in some cases. That is, for example, a mass loss ratio at a high temperature of 300° C. is increased in some cases. Furthermore, since the known D-BMI contains an active maleimide group at a large amount, for example, when it is used as a component of a composition for a sealing material of a semiconductor, by blending it with another thermosetting resin, for example, an epoxy resin, a phenol resin, a cyanate resin, a benzoxazine resin or the like, control of a thermosetting reaction becomes difficult, and processing is deteriorated in some cases. Then, the present invention solves the above-mentioned problem, and an object thereof is to provide a D-BMI modified product with the sufficiently enhanced heat resistance and processability.

Means to Solve the Problems

It was found out that the above-mentioned problem is solved by considerably reducing an acid value of D-BMI and, thereafter, modifying the D-BMI into a specific chemical structure defined by NMR, resulting in completion of the present invention.

The present invention features the following:
<1> A D-BMI Modified Product having the Following Characteristics:
1) An acid value of the D-BMI modified product is 2 mg-KOH/g or less.
2) In $^1$H-NMR, when quantitative comparison is performed using an integrated value (A) of a peak corresponding to a proton of a methylene group directly bound to a nitrogen atom of a maleimide group and an integrated value (B) of a peak corresponding to a vinyl proton of a maleimide group, A/B is 1.25 or more and 2.00 or less.
<2> A Method for Producing D-BMI of claim 1, the Method Including the Following Steps:
1) A step of preparing a crude D-BMI solution having an acid value of more than 2 mg-KOH/g.
2) A step of lowering an acid value of D-BMI to 2 mg-KOH/g or less by reacting an acid component in the solution with a carbodiimide (CDI).
3) A step of reacting the solution without a catalyst at 110 to 200° C. in a solvent.

Effects of the Invention

Since in the D-BMI modified product of the present invention, an acid component has been sufficiently reduced, the sufficient heat resistance is secured, and since the content of a maleimide group is made to be in a moderate range, the processability is good. Accordingly, the D-BMI modified product can be suitably used as a component of a sealing material composition, an adhesive composition or the like, which is used in manufacturing electronic parts using a semiconductor or the like.

BRIEF DESCRIPTION OF THE DRAWINGS

FIG. 1 A $^1$H-NMR chart of D-BMI before modification (Example 1).
FIG. 2 A $^1$H-NMR chart of the D-BMI modified product of the present invention (Example 1).

MODE FOR CARRYING OUT THE INVENTION

The D-BMI modified product of the present invention is obtained by lowering an acid value to 2 mg-KOH/g or less, and chemically modifying D-BMI. Herein, the acid value is a parameter quantitatively expressing an amount of an acid component remaining in the D-BMI, and a value measured by a neutralization titration method based on the provision of JIS K0070 (1992) can be used. D-BMI having an acid value of 2 mg-KOH/g or less can be obtained by purifying a D-BMI solution having an acid value of more than 2 mg-KOH/g, which has been obtained by the known method. The D-BMI solution having an acid value of more than 2 mg-KOH/g can be obtained, for example, by the following method. That is, a crude D-BMI solution having an acid value of more than 2 mg-KOH/g can be obtained by reacting DDA and an approximately equal equivalent of maleic anhydride at a temperature of 50 to 200° C. under an acid catalyst in a solvent to obtain MAA, and thereafter, dehydrating to maleimidize the MAA. A solvent used herein is not limited, but a hydrocarbon solvent such as toluene, xylene (o-xylene, m-xylene, p-xylene), ethylbenzene, mesitylene, and solvent naphtha, an amide solvent such as N-methyl-2-pyrrolidone (NMP), N,N-dimethylformamide (DMF), and N,N-dimethylacetamide (DMAc), a mixed solvent of a hydrocarbon solvent and an amide solvent, and the like are preferable. Additionally, the acid catalyst used is also not limited, but sulfuric acid, methanesulfonic acid, benzenesulfonic acid, orthophosphoric acid, metaphosphoric acid, pyrophosphoric acid, phosphorous acid, hypophosphorous acid, maleic acid, and the like can be used. Triethylamine salts of these acids can also be used. When dehydration for ring closure is performed, it is preferable to remove water generated by maleimidization to the outside of the reaction system by azeotropy or the like. Herein, as DDA, commercial products such as "Priamine 1074, the same 1075" (trade name made by Croda Japan KK), and "Versamine 551, the same 552" (trade name made by Cognis Japan Ltd.) can be used. In addition, as a crude D-BMI solution, commercial products can also be used.

The crude D-BMI may be the above-mentioned crude D-BMI using DDA alone, and it is also preferable to use "imide-extended DDA" as described in Patent Documents 10 and 11. Herein, "imide-extended DDA" is "polyimide or oligoimide having an amino group derived from DDA at both ends" which is obtained by reacting a tetracarboxylic dianhydride with an excessive amount of DDA to perform dehydration and ring closure. Specific examples of tetracarboxylic dianhydride include pyromellitic dianhydride (PMDA), 3,3',4,4'-diphenyltetracarboxylic dianhydride (BPDA), 2,3,3',4'-biphenyltetracarboxylic dianhydride, 3,3', 4,4'-benzophenonetetracarboxylic dianhydride, 4,4'-oxydiphthalic anhydride (ODPA), 2,2-bis(3,4-dicarboxyphenyl) propane dianhydride (BDCP), 3,3',4,4'-diphenylsulfontetracarboxylic dianhydride, and the like. These may be used alone, or may be used by combining two or more of them. As the crude D-BMI using this "imide-extended DDA", commercial products can also be used.

Then, the crude D-BMI obtained as described above is purified to obtain D-BMI having an acid value of 2 mg-KOH/g or less. That is, CDI such as N,N'-diisopropylcarbodiimide (DIC), and 1-ethyl-3-(3-dimethylaminopropyl) carbodiimide (EDC) is added at 1 to 10% by mass to the mass of D-BMI in a solvent, and heated to a temperature of 50° C. to 150° C., thereby, an acid component in D-BMI and CDI are reacted to lower an acid value of D-BMI to 2 mg-KOH/g or less. Upon this reaction, the solid matter concentration of crude D-BMI is preferably 20 to 70% by mass, and more preferably 30 to 80% by mass, to the mass of a solution. By this reaction, an acid component in D-BMI and CDI are reacted, and a urea derivative of CDI is produced as a byproduct. This urea derivative of CDI can be removed by washing the reaction solution with water, an alcohol (methanol, ethanol etc.) or the like, that is, by performing solvent extraction. In this way, D-BMI having an acid value of 2 mg-KOH/g or less can be obtained. An acid value of purified D-BMI is preferably 1 mg-KOH/g or less, and further preferably 0.5 mg-KOH/g or less. By doing this, the good heat resistance of D-BMI can be secured.

A solvent used in this reaction is not limited, but a hydrocarbon solvent such as toluene, xylene (o-xylene, m-xylene, p-xylene), ethylbenzene, mesitylene, and solvent naphtha is preferable. Additionally, as CDI used in this reaction, the above-mentioned DIC or EDC is preferable, and as other CDI, bis(2,6-diisopropylphenyl)carbodiimide, diphenylcarbodiimide, di-P-naphthylcarbodiimide, dimethylcarbodiimide, diisobutylcarbodiimide, dioctylcarbodiimide, t-butylisopropylcarbodiimide, di-t-butylcarbodiimide, N,N'-dicyclohexylcarbodiimide (DCC), poly(1,6-hexamethylenecarbodiimide), poly(4,4'-methylenebiscyclohexylcarbodiimide), poly(1,3-cyclohexylenecarbodiimide), poly(1,4-cyclohexylenecarbodiimide), poly(4,4'-dicyclohexylmethanecarbodiimide), poly(4,4'-diphenylmethanecarbodiimide), poly(3,3'-dimethyl-4,4'-diphenylmethanecarbodiimide), poly(naphthylenecarbodiimide), poly(p-phenylenecarbodiimide), poly(m-phenylenecarbodiimide), poly(tolylcarbodiimide), poly(methyl-diisopropylphenylenecarbodiimide), poly(1,3,5-triisopropylbenzenecarbodiimide), poly(1,3,5-triisopropylbenzene and 1,5-diisopropylbenzenecarbodiimide), poly(triethylphenylenecarbodiimide), poly(triisopropylphenylenecarbodiimide), poly(diisopropylcarbodiimide), and the like can also be used. These CDIs may be used alone, or may be used by combining two or more of them.

The D-BMI modified product of the present invention can be obtained by reacting D-BMI having an acid value of 2 mg-KOH/g or less, which was obtained as described above, at 110 to 200° C., preferably 130 to 180° C. in a solvent, under stirring, without using a catalyst. In this reaction, it is preferable to heat the reactants substantially without using a catalyst. When the reactants are heated in the presence of an acid catalyst as described above, a reaction does not progress effectively in some cases. A solvent used in this reaction is not limited, but the above-mentioned hydrocarbon solvents are preferably used, and among them, toluene and xylene are particularly preferable. The D-BMI concentration upon a reaction is preferably 30 to 90% by mass, more preferably 40 to 85% by mass, and further preferably 50 to 80% by mass. When the D-BMI concentration is less than 30% by mass, a reaction does not progress effectively in some cases. On the other hand, when the D-BMI concentration exceeds 90% by mass, control of a reaction becomes difficult in some cases. By this heating reaction, a maleimide group which is an active group of D-BMI is modified by a complicated reaction such as linear vinyl polymerization and a cyclization reaction, and the D-BMI modified product of the present invention can be obtained. In addition, this solution can be used as it is as a D-BMI modified product solution. Alternatively, by volatilizing a solvent, the modified product can be isolated as a single product.

As for the thus obtained D-BMI modified product, it is necessary that a NMR integrated value ratio (A/B) in $^1$H-NMR thereof is 1.25 or more and 2.00 or less, and the ratio is preferably 1.30 or more and 1.80 or less. Herein, A is an integrated value of a peak corresponding to a proton of a methylene group directly bound to a nitrogen atom of a maleimide group, and B is an integrated value of a peak corresponding to a vinyl proton of a maleimide group. By doing this, since the content of a maleimide group has become suitable, control of a reaction when another thermosetting resin is blended becomes easy. That is, when a NMR integrated value ratio is less than 1.25, control of a reaction when another thermosetting resin is blended becomes difficult. In addition, when a NMR integrated value ratio exceeds 2.00, the modified product is brought into the semi-gel state (so-called B stage state), and solubility in the above-mentioned solvents is deteriorated in some cases, being not preferable.

Herein, the NMR measuring conditions are as follows:

<$^1$H-NMR Measurement Conditions>
Apparatus: Nuclear magnetic resonance apparatus (made by JEOL Ltd.: Model Number ECA500)
Frequency: 500.16 MHz
Standard substance: Tetramethylsilane
Solvent: Deuterated chloroform
Measurement temperature: 25° C.

Under the above-mentioned measuring conditions, the chemical shift corresponding to a peak of a proton of a methylene group directly bound to a nitrogen atom of a maleimide group in D-BMI or the D-BMI modified product is about 3.5 ppm. Additionally, the chemical shift corresponding to a peak of a vinyl proton of a maleimide group in D-BMI or the D-BMI modified product is about 6.7 ppm. Accordingly, by reading integrated values of these peaks from a NMR chart, the NMR integrated value ratio can be calculated. Herein, it is meant that as the NMR integrated value ratio is higher, the content of a maleimide group in the D-BMI modified product is lower, and by adjusting this NMR integrated value ratio at 1.25 or more and 2.00 or less, the good processability can be secured when used by blending the modified product together with an epoxy resin, a phenol resin or the like.

By adjusting the NMR integrated value ratio at 1.25 or more and 2.00 or less, a molecular weight of D-BMI can be remarkably increased as compared with that before modification. A rate of increase in a molecular weight is preferably 10% or more and 500% or less. It is preferable that a molecular weight of the thus obtained D-BMI modified product of the present invention is in a range of 1,200 to 20,000 as expressed by a weight average molecular weight (Mw). By adjusting Mw of the D-BMI modified product in such a range, the above-mentioned good processability can be secured. In addition, Mw can be confirmed, for example, by measuring GPC under the following conditions:

<GPC Measuring Conditions>
Column: Shodex (R) made by SHOWA DENKO K.K., GPC KF-803× one column, GPC KF-804 x two columns (three columns are coupled)
Elute: THF
Temperature: 40° C.
Flow rate: 1.0 mL/min
Detector: UV detector

EXAMPLES

The present invention will be illustrated in further detail below by way of examples. In addition, the present invention is not limited by examples.

Example 1

1) Preparation of Crude D-BMI Solution

In accordance with the description of Example 1 in Patent Document 11, a crude D-BMI solution was prepared. Dimer diamine ("Priamine 1075" made by Croda Japan KK, molecular weight: 549): 1.0 mole, and a mixed solvent consisting of toluene and DMAc (ratio by mass: toluene/DMAc=80/20) were placed into a glass reactor vessel equipped with a reflux condenser with a water separator, a stirrer, and a thermometer under the nitrogen atmosphere, and stirred. To the resulting solution were added PMDA: 0.66 mole, and subsequently, maleic anhydride: 0.68 mole at room temperature (20° C.), the mixture was stirred at room temperature for 1 hour, heated at 80° C. for 3 hours, and cooled to obtain a solution of an oligoamic acid in which the end was maleamic acid-modified (solid matter concentration: 40% by mass). Then, to this solution was added 2.00 mole of maleic acid, and a temperature was raised while the resulting solution was stirred, to heat-reflux the content. Reflux was continued at about 115° C. for 6 hours while water generated by the reaction was separated by azeotropy, and thereafter, the reaction solution was cooled to obtain an orangish-yellow solution. Thereafter, the resulting solution was washed with an aqueous solvent five times. Subsequently, this solution was placed into a methanol solution to re-precipitate D-BMI, which was filtered, washed, and dried. This operation was repeated two times to obtain a powder of D-BMI. This powder was dissolved in toluene to obtain a crude D-BMI solution having the solid matter concentration of 40% by mass. An acid value of this crude D-BMI was 7.83 mg-KOH/g.

2) Reduction in Acid Value by CDI

Into a glass reactor vessel equipped with a stirrer and a thermometer were placed the above-mentioned crude D-BMI solution: 200 g, and N,N'-diisopropylcarbodiimide (DIC): 4 g under the nitrogen atmosphere, and the mixture was stirred. To the resulting solution were added PMDA: 0.66 mole, and subsequently, maleic anhydride: 0.68 mole at room temperature (20° C.), and the mixture was stirred at room temperature for 1 hour, heated at 70° C. for 5 hours, and cooled to obtain an orangish-yellow solution. Thereafter, the resulting solution was washed with methyl alcohol three times, and thereby, a purified D-BMI solution was obtained. Results of measurement of $^1$H-NMR thereof under the above-mentioned conditions are shown in FIG. 1. As shown in FIG. 1, quantitative comparison was performed using an integrated value (A) of a peak 1 (8: about 3.5 ppm multiplet) and an integrated value (B) of a peak 2 (8: about 6.7 ppm singlet) recognized in this $^1$H-NMR chart, and as a result, A/B was 1.19. Additionally, an acid value of this D-BMI was 0.26.

3) Modification of D-BMI

A toluene solution of the above-mentioned D-BMI having the solid matter concentration of 50% by mass of the entire solution was placed into a glass reactor vessel equipped with a thermometer under the nitrogen atmosphere, and stirred. Thereafter, the mixture was stirred at 130° C. for 4 hours to obtain an orangish-yellow uniform solution containing a D-BMI modified product (A-1). Results of measurement of $^1$H-NMR thereof under the above-mentioned conditions are shown in FIG. 2. As shown in FIG. 2, quantitative comparison was performed using an integrated value (A) of a peak 1 (δ: about 3.5 ppm multiplet) and an integrated value (B) of a peak 2 (δ: about 6.7 ppm singlet) recognized in this $^1$H-NMR chart, and as a result, A/B was 1.29. Additionally, an acid value of this D-BMI was 0.25. In addition, from comparison of $^1$H-NMR between FIG. 1 and FIG. 2, it is seen that in a D-BMI modified product obtained by heating, other than reduction in a vinyl proton of a maleimide group, a significant change in a chemical structure has not occurred.

<Molecular Weight Assessment>

Mw of D-BMI before modification and A-1 was measured by the above-mentioned method, and a rate of increase in a molecular weight was calculated to assess a change in a molecular weight. Results are shown in Table 1.

<Heat Resistance Assessment>

Heat resistance assessment of A-1 was performed as follows. That is, about 5 mg of a 50 mass % toluene solution of A-1 was placed in a sample pan made of platinum, this was set in a TGA measuring apparatus (TG/DTA7200 made by Hitachi High-Tech Corporation), toluene was removed at 130° C. in a nitrogen stream, thereafter, a rate of decrease in the mass at 300° C. when a temperature was raised to 550° C. at 10° C./min was read, and thereby, the heat resistance was assessed. Results thereof are shown in Table 1.

Example 2

According to the same manner as that of Example 1 except that a reaction temperature upon modification was 140° C., a uniform solution containing a D-BMI modified product (A-2) was obtained. Results of assessment of an acid value, NMR quantitative comparison, a molecular weight, and the heat resistance of A-2 are shown in Table 1.

Example 3

According to the same manner as that of Example 1 except that a use amount of DIC was 3.5 g, and a reaction temperature upon modification was 145° C., a uniform solution containing a D-BMI modified product (A-3) was obtained. Results of assessment of an acid value, NMR quantitative comparison, a molecular weight, and the heat resistance of A-3 are shown in Table 1.

Example 4

According to the same manner as that of Example 1 except that the D-BMI concentration was 65% by mass, a uniform solution containing a D-BMI modified product (A-4) was obtained. Results of assessment of an acid value, NMR quantitative comparison, a molecular weight, and the heat resistance of A-4 are shown in Table 1.

Example 5

D-BMI (made by DMI company: Model Number BMI-689) (100 g) was dissolved in 100 g of toluene to obtain a crude D-BMI solution having the solid matter concentration of 40% by mass. An acid value of this crude D-BMI was 4.72 mg-KOH/g.

This solution was subjected to purification by DIC, and modification by heating at 130° C. as in Example 1, and a uniform solution containing a D-BMI modified product (A-5) was obtained. Results of assessment of an acid value, NMR quantitative comparison, a molecular weight, and the heat resistance of A-5 are shown in Table 1. In addition, BMI-689 is D-BMI containing only DDA as a diamine component.

Example 6

According to the same manner as that of Example 5 except that a reaction temperature upon modification was 140° C., a uniform solution containing a D-BMI modified product (A-6) was obtained. Results of assessment of an acid value, NMR quantitative comparison, a molecular weight, and the heat resistance of A-6 are shown in Table 1.

Example 7

According to the same manner as that of Example 5 except that a use amount of DIC upon purification was 3 g, a uniform solution containing a D-BMI modified product (A-7) was obtained. Results of assessment of an acid value, NMR quantitative comparison, a molecular weight, and the heat resistance of A-7 are shown in Table 1.

Comparative Example 1

Without purifying the crude D-BMI obtained in Example 1, a uniform solution containing D-BMI (B-1) (concentration: 50% by mass) was obtained. Results of assessment of an acid value, NMR quantitative comparison, a molecular weight, and the heat resistance of B-1 are shown in Table 1.

Comparative Example 2

Without modifying the purified D-BMI obtained in Example 1, a uniform solution containing D-BMI (B-2) (concentration: 50% by mass) was obtained. Results of assessment of an acid value, NMR quantitative comparison, a molecular weight, and the heat resistance of B-2 are shown in Table 1.

Comparative Example 3

Without purifying the D-BMI (made by DMI company: Model Number BMI-689) used in Example 5, a uniform solution containing D-BMI (B-3) (concentration: 50% by mass) was obtained. Results of assessment of an acid value, NMR quantitative comparison, a molecular weight, and the heat resistance of B-3 are shown in Table 1.

Comparative Example 4

Without modifying the purified D-BMI obtained in Example 5, a uniform solution containing D-BMI (B-4) (concentration: 50% by mass) was obtained. Results of assessment of an acid value, NMR quantitative comparison, a molecular weight, and the heat resistance of B-4 are shown in Table 1.

Comparative Example 5

According to the same manner as that of Example 5 except that a reaction temperature upon modification was 100° C., a uniform solution containing D-BMI (B-5) (concentration: 50% by mass) was obtained. Results of assessment of an acid value, NMR quantitative comparison, a molecular weight, and the heat resistance of B-5 are shown in Table 1.

Comparative Example 6

According to the same manner as that of Example 1 except that a reaction temperature was 190° C., and the D-BMI concentration was 95% by mass, an attempt to obtain a D-BMI modified product was made, but gelling was caused, and a D-BMI modified product could not be obtained.

Since in D-BMI of the present invention, an acid value has been sufficiently reduced as shown in examples, it is seen that the heat resistance is considerably improved. Additionally, it is seen that an integrated value ratio of NMR is in an appropriately range, a weight average molecular weight (Mw) is considerably increased.

TABLE 1

| | D-BMI modified product | Acid value (mg-K OH/g) | NMR quantitative comparison (A/B) | Molecular weight (Mw) | Rate of increase in molecular weight (%) | Rate of decrease in mass (%) |
|---|---|---|---|---|---|---|
| Example 1 | A-1 | 0.25 | 1.29 | 8900 | 43.3 | 0.11 |
| Example 2 | A-2 | 0.35 | 1.41 | 9750 | 57.0 | 0.18 |
| Example 3 | A-3 | 0.32 | 1.52 | 12400 | 99.7 | 0.15 |
| Example 4 | A-4 | 0.38 | 1.63 | 16500 | 181.8 | 0.26 |
| Example 5 | A-5 | 0.46 | 1.28 | 1860 | 69.1 | 0.35 |
| Example 6 | A-6 | 0.45 | 1.57 | 4520 | 310.9 | 0.31 |
| Example 7 | A-7 | 0.40 | 1.35 | 2190 | 99.1 | 0.21 |
| Comparative Example 1 | B-1 | 7.83 | 1.19 | 6210 | 0.0 | 1.08 |
| Comparative Example 2 | B-2 | 0.26 | 1.21 | 6280 | 0.1 | 0.15 |
| Comparative Example 3 | B-3 | 4.72 | 1.10 | 1100 | 0.0 | 0.86 |
| Comparative Example 4 | B-4 | 0.42 | 1.12 | 1150 | 4.5 | 0.36 |
| Comparative Example 5 | B-5 | 0.46 | 1.17 | 1180 | 7.3 | 0.41 |

INDUSTRIAL APPLICABILITY

Since an acid component of the D-BMI modified product of the present invention has been sufficiently reduced, the sufficient heat resistance is secured, and since the content of a maleimide group is adjusted in an appropriate range, the processability is good. Accordingly, the modified product can be suitably used as a component of a sealing composition, an adhesive composition, and the like, which are used in manufacturing electronic parts using a semiconductor or the like.

The invention claimed is:

1. A bismaleimide (D-BMI) modified product in which an amino group of dimer diamine is maleimidized, the bismaleimide modified product having the following characteristics:
   1) In $^1$H-NMR, when quantitative comparison is performed using an integrated value (A) of a peak corresponding to a proton of a methylene group directly bound to a nitrogen atom of a maleimide group and an integrated value (B) of a peak corresponding to a vinyl proton of a maleimide group, A/B is 1.25 or more and 2.00 or less; and
   2) A weight average molecular weight of the D-BMI modified product is in a range of 1,200 to 20,000.

* * * * *